(12) United States Patent
Chuang et al.

(10) Patent No.: US 9,505,001 B2
(45) Date of Patent: Nov. 29, 2016

(54) POROUS FILM MICROFLUIDIC DEVICE FOR AUTOMATIC SURFACE PLASMON RESONANCE QUANTITATIVE ANALYSIS

(71) Applicant: National Taiwan University, Taipei (TW)

(72) Inventors: Tsung-Liang Chuang, Taipei (TW); Chii-Wann Lin, Taipei (TW); Chia-Chen Chang, Taipei (TW); Shih-Chung Wei, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 53 days.

(21) Appl. No.: 14/242,242

(22) Filed: Apr. 1, 2014

(65) Prior Publication Data

US 2015/0010916 A1     Jan. 8, 2015

(30) Foreign Application Priority Data

Jul. 2, 2013    (TW) .............................. 102123597 A

(51) Int. Cl.
    *B01L 3/00*                  (2006.01)

(52) U.S. Cl.
    CPC ........ *B01L 3/502715* (2013.01); *B01L 3/5023* (2013.01); *B01L 2300/044* (2013.01);
(Continued)

(58) Field of Classification Search
    CPC ........... G01N 21/648; G01N 21/7703; G01N 21/553; G01N 33/54373; G01N 21/554; G01N 21/658; G01N 33/558; G01N 2021/056; G01N 21/65; G01N 33/553; Y10S 435/805; Y10S 435/97; Y10S 436/805; B01L 2200/10; B01L 2300/0636; C12Q 2565/632; C12Q 2537/125; C12Q 2563/155; C12Q 2565/628
See application file for complete search history.

(56) References Cited

U.S. PATENT DOCUMENTS 6,104,484 A * 8/2000 Nagata ................. G01N 21/553
                                                     356/246
6,127,129 A * 10/2000 Corn et al. ................... 435/6.19
(Continued)

FOREIGN PATENT DOCUMENTS

CN        101389947 A     3/2009
TW        201329230 A     7/2013
(Continued)

OTHER PUBLICATIONS

Moreira et al. "Exchangeable low cost polymer biosensor chip for surface plasmon resonance spectroscopy", Procedia Chemistry, 1 (2009) 1479-1482.*
(Continued)

*Primary Examiner* — Erik B Crawford
(74) *Attorney, Agent, or Firm* — Muncy, Geissler, Olds & Lowe, P.C.

(57) ABSTRACT

A porous film microfluidic device includes a sample well, a porous film support structure, including a first, second, and third port, wherein the first port is connected to the sample well, a porous film is formed over the bottom of the porous film support structure, and a glass fiber film is formed between the porous film support structure and the porous film, a waste tank connected to the second port of the porous film support structure, wherein a water absorption element is disposed in the waste tank, a buffer solution tank connected to the third port of the porous film support structure and sealed by a sealing film, and a COC plastic prism disposed over the bottom of the porous film support structure. The COC plastic prism includes a metal film in contact with the porous film and a metal oxide layer formed over the COC plastic prism.

9 Claims, 4 Drawing Sheets

(52) U.S. Cl.
CPC ... *B01L2300/069* (2013.01); *B01L 2300/0636* (2013.01); *B01L 2300/0654* (2013.01); *B01L 2300/0816* (2013.01); *B01L 2300/168* (2013.01); *B01L 2400/0406* (2013.01); *G01N 2333/57* (2013.01)

(56) References Cited

U.S. PATENT DOCUMENTS

| | | | |
|---|---|---|---|
| 7,074,621 B2* | 7/2006 | Latov et al. | 436/518 |
| 2005/0244985 A1* | 11/2005 | Freitag | B01L 3/5023 436/514 |
| 2009/0253119 A1* | 10/2009 | Zhou | G01N 33/558 435/5 |
| 2010/0230284 A1 | 9/2010 | Stephenson | |
| 2011/0204084 A1* | 8/2011 | Aronowitz | 222/1 |
| 2012/0040470 A1* | 2/2012 | Dorn et al. | 436/169 |
| 2015/0064800 A1* | 3/2015 | Chance et al. | 436/501 |

FOREIGN PATENT DOCUMENTS

| | | |
|---|---|---|
| WO | 2005088300 A | 9/2005 |
| WO | 2007075444 A | 7/2007 |

OTHER PUBLICATIONS

Chang et al. "High-Sensitivity Detection of Carbohydrate Antigen 15-3 Using a Gold/Zinc Oxide Thin Film Surface Plasmon Resonance-Based Biosensor", Anal. Chem, 2010, 82, 1207-1212.*

* cited by examiner

POROUS FILM MICROFLUIDIC DEVICE FOR AUTOMATIC SURFACE PLASMON RESONANCE QUANTITATIVE ANALYSIS

CROSS REFERENCE TO RELATED APPLICATION

This application claims the benefits of the Taiwan Patent Application Serial Number 102123597, filed on Jul. 2, 2013, the subject matter of which is incorporated herein by reference.

BACKGROUND OF THE INVENTION

1. Field of the Invention

The present invention relates to a porous film microfluidic device, and particularly to a porous film microfluidic device for automatic surface plasmon resonance quantitative analysis.

2. Description of Related Art

In the field of chip detection technology, detection is generally realized by changes in optical signals, in particular fluorescence signals. Although most changes in fluorescence signals are conveniently observable to the naked eye, it however, lacks sufficient sensitivity. Recently, in order to enhance the detection sensitivity, a change in the intensity of the reflected light due to the surface plasmon resonance (SPR) phenomenon has been served as the basis of the detection. As for the detection of a biological sample, biomolecules are attached to a gold (Au) or silver (Ag) film and the binding between the sample and the metal film is determined by detecting the change in the intensity of reflected light before and after the binding, which provides a high detecting discrimination.

Currently, some technologies use SPR as a platform to incorporate microfluidic chips to detect the biological or chemical samples. According to the currently known microfluidic chip technology, an external force, typically exerted by a pump is used to inject the sample into the microfluidic channel to combine with the biomolecules. The necessity for using a pump brings much inconvenience to chip detection. Specifically, the known microfluidic chip may not be applicable to detect a trace amount of sample from an animal or a plant because the sample volume is too little to be injected into the microfluidic channel. Besides, a high evaporation rate of these samples may be another technical barrier for detection, and thus, the application of the known microfluidic chip will be limited.

In order to effectively achieve cost reduction and the convenience of use outside the laboratory, a microfluidic platform with lateral flow test strips has been proposed. However, the sample in the conventional microfluidic platform with lateral flow test strips easily evaporates, and a multi-step processes cannot be conducted. As a result, the improvement on the detection sensitivity of detection of a trace amount of sample is not possible, and the detection accuracy can be reduced easily.

In view of the above drawbacks, what is needed is to develop a microfluidic chip, by which a trace amount of sample can be injected without using a pump and with a reduced evaporation rate, to thereby increase its maneuverability and expand its applications.

SUMMARY OF THE INVENTION

An objective of the present invention is to provide a porous film microfluidic device, in which a trace amount of sample may flow to the sensing area through a natural force, without the use of a pump, and SPR signal of the sample is detected under a low evaporation rate.

Another object of the present invention is to provide a quantitative detection system convenient for users, so as to improve the detection efficiency of the conventional microfluidic devices and the instability of the lateral flow agent.

To achieve the above object, the present invention provides a porous film microfluidic device, comprising: a sample well; a porous film support structure, which comprises a first port having a depth of 200-500 μm, and preferably 300-400 μm, as well as a width of 1-2 mm, and preferably 1.2-1.8 mm, a second port and a third port, wherein the first port is connected to the sample well, a porous film is formed over the bottom of the porous film support structure, and a glass fiber film attached with a chemical agent is formed between the porous film support structure and the porous film; a waste tank connected to the second port of the porous film support structure, wherein a water absorption element is disposed in the waste tank, and a distance between the water absorption element and the porous film is 200-400 μm, and preferably 200-300 μm; a buffer solution tank connected to the third port of the porous film support structure and sealed by a sealing film; and a COC (cycloolefin copolymer) plastic prism disposed on the bottom of the porous film support structure, wherein the COC plastic prism comprises a metal film attached with a bio-molecule and in contact with the porous film, and a metal oxide layer is formed on the COC plastic prism and between the metal film and COC plastic prism. Herein, a sample flows from the sample well into the porous film support structure to reach the metal film by a natural force, and the target analyte in the sample to be detected is combined with a biomolecule on the metal film, and the sample injection is stopped at the balance of the natural force. In addition, a buffer solution flows from the buffer solution tank into the porous film support structure through the third port to reach the metal film by the natural force, thereby washing the excess sample that fails to combine with the biomolecule.

Chemical reagents to be mixed with the sample are carried on the above glass fiber film for the adsorption and release of nano-molecule, such as a plasmid or a gold nanoparticle, etc., depending on the particular application.

In the porous film microfluidic device, the volume of the sample is not particularly limited, and may be 5 μl to 10 μl, and preferably 7 μl to 10 μl. The concentration of the sample is not particularly limited, and may be 0.01 nM to 500 nM, preferably 0.03 nM to 200 nM, and more preferably 0.1 nM to 100 nM. In addition, the porous film has a volume of 5 μl to 10 μl.

In the porous film microfluidic device, the material of the sample is not particularly limited, and preferably a nitrocellulose film, a filament film or a non-woven fabric having a pore size of more than 10 to 500 μm, wherein the nitrocellulose may be, for example, hydrophilic wood pulp fiber, hydrophilic PVA fiber, and so on.

In the microfluidic device, the material of the metal film may be any metal suitable for SPR detection, such as gold (Au) or silver (Ag). The material of the metal oxide film may be a transparent material, such as zinc oxide (ZnO), and preferably exhibit adhesion to the metal film and the plastic. In addition, the biomolecule on the metal film may be DNA, RNA, a protein, an antibody, or the combinations thereof, which may be selected depending on the detection requirements, such as IFN-γ antibody. Basically, the metal film attached with the biomolecule may be in various forms, such as a metal film array and so on.

In the microfluidic device, the waste tank is sealed by a sealing film. The material of the water absorption element is not particularly limited, and may be PVA foam, non-woven fabric, drawing paper, absorbent paper, and the like, and preferably PVA foam or non-woven fabric. In addition, the size of the water absorption element is not particularly limited, as long as the water absorption element can be accommodated in the waste tank, and preferably can swell after absorbing water. In the present invention, the distance between the water absorption element and the porous film is 200-500 μm, and preferably 300-400 μm. According to the design of the chip of present invention, one advantage of the present invention is that the water absorption element can achieve the driving of the fluid flow without a direct contact with the porous film.

Due to the design of the above microfluidic device, the sample may flow into the microfluidic channel by a natural force without an external force provided by a pump. Herein, the natural force refers to a non-man-made force, such as a capillary force generated by the capillary effect of the porous film; a pressure resulted from a hydraulic pressure difference in the waste tank, a gravity force of the sample itself, an atmospheric pressure on the sample, and the like.

To achieve another object of the present invention, the present invention provides a method for detecting a micro sample by a porous film microfluidic device, comprising the following steps: (A) providing the above-mentioned porous film microfluidic device, (B) injecting a sample into the sample well, and the sample flows into the porous film of the porous film support structure to contact the metal film, wherein when the sample is static in the porous film, it can soak the glass fiber to release a chemical agent thereon; (C) opening the sealing film such that the buffer solution flows into the porous film of the porous film support structure to wash the metal film, thereby washing out the excess sample from the metal film to prevent the detection from noise interference and (D) detecting a surface plasmon resonance (SPR) signal of the metal film.

In the step (B), the sample is driven by absorption of the porous film and a hydraulic pressure difference between the sample well and the waste tank, and flows into the porous film of the porous film support structure, to reach the metal film, such that the target analyte in the sample is combined with a biomolecule of the metal film.

Furthermore, in the step (C), the buffer solution is driven by absorption of the porous film and a hydraulic pressure difference between the buffer solution tank and the waste tank, and flows into the porous film of the porous film support structure, to thereby wash the metal film.

In the method of the present invention, due to the special design of the microfluidic device, the evaporation rate of the porous film sample is reduced such that the sample can be maintained in the porous film support structure for 45 minutes. Therefore, the detection time in the step (D) may be between 1-45 minutes, thereby enhancing detection accuracy by prolongation of the detection time, compared to conventional techniques.

As for the surface plasmon resonance microfluidic device provided in the step (A) of the present invention, the definition of "natural force", the sample volume, the sample concentration, the material of the porous film, the biological molecule, the material of the metal film and the water absorption element have been described above, and thus will not be repeated here.

The microfluidic device of the present invention is used to detect the SPR signals of samples having a steady state in the microfluidic channel. Conventionally, the flow rate of sample in the microfluidic channel is controlled by a pump. However, in the present invention, due to the special design of the microfluidic device, the sample can be automatically transferred to the sensing area, and stops flowing when a balance of the pressure and the absorption force of the porous film is reached, and therefore the flow of the sample in the chip can be controlled without an external pressure at all. Thus, compared to prior art, the present invention has achieved a breakthrough on the detection convenience. Further, a porous material is further included at the bottom of the microfluidic channel according to the present invention, not only to quantify the sample, but also to prolong the residence time of the sample in the microfluidic channel, and to slow the evaporation rate, thereby increasing the detection accuracy. Therefore, the present invention is particularly suitable for the quantitative detection of samples in low resources conditions. Accordingly, compared to prior art, the microfluidic device of the present invention achieves a substantial breakthrough on the limitations imposed by the sample volume and concentration.

DETAILED DESCRIPTION OF THE PREFERRED EMBODIMENT

The present invention will now be explained in further detail with reference to the following examples. However, these examples are merely illustrative of the present invention, the scope of which shall not be construed to be limited by the following examples.

Example 1

Figure 1:
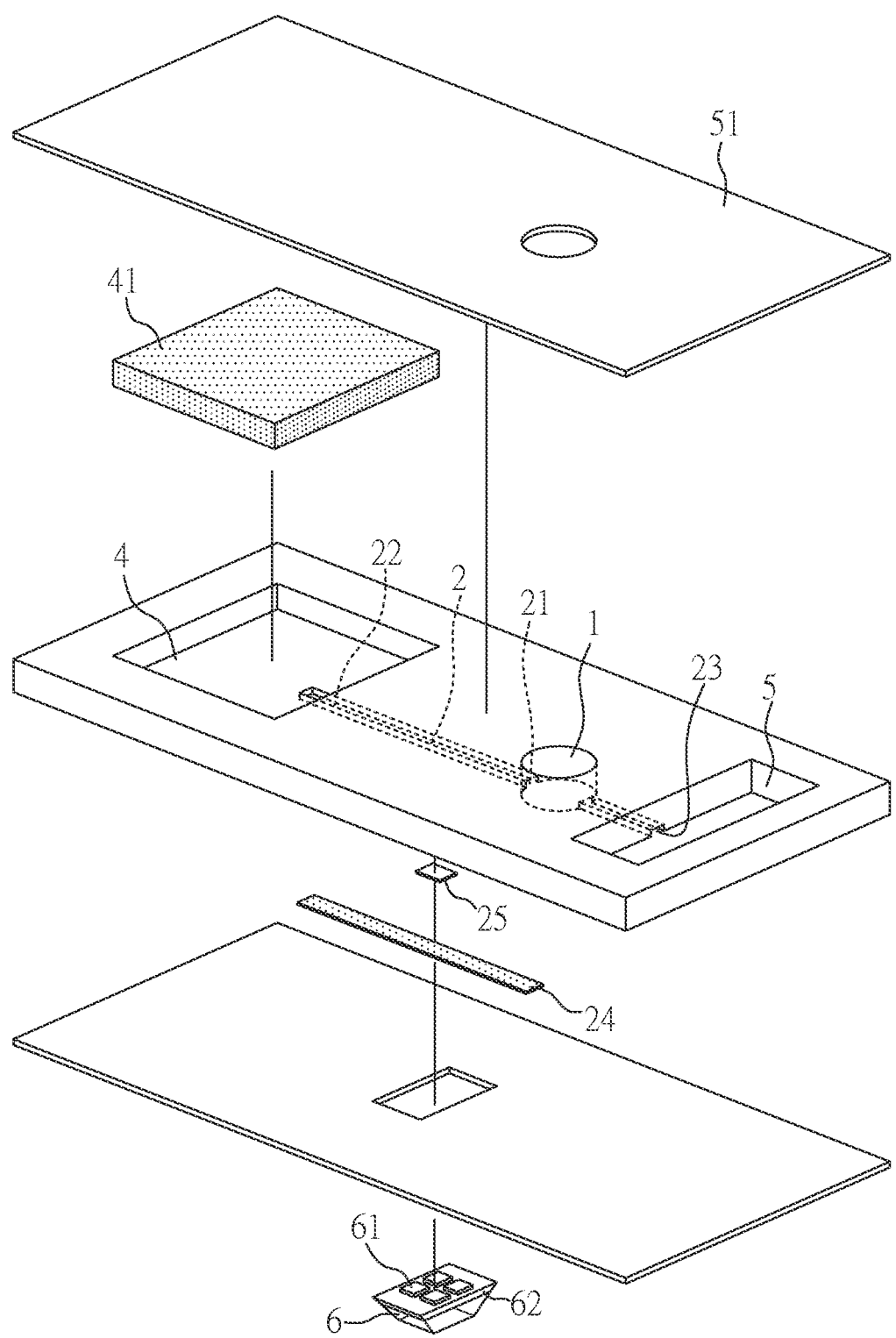
FIG. 1 shows an exploded view of the porous film microfluidic device according to Example 1 of the present invention.
Figure 2:
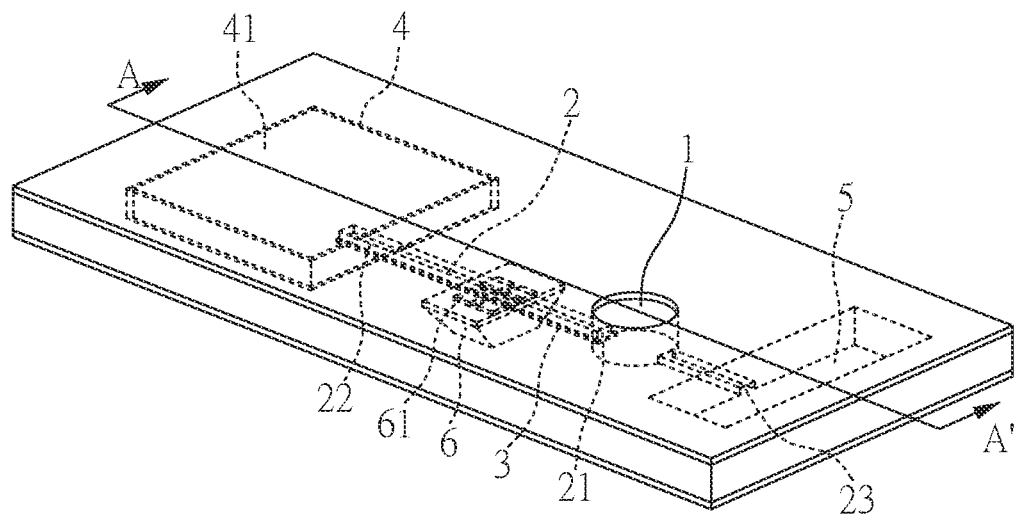
FIG. 2 shows a schematic view of the porous film microfluidic device according to Example 1 of the present invention.
Figure 3:
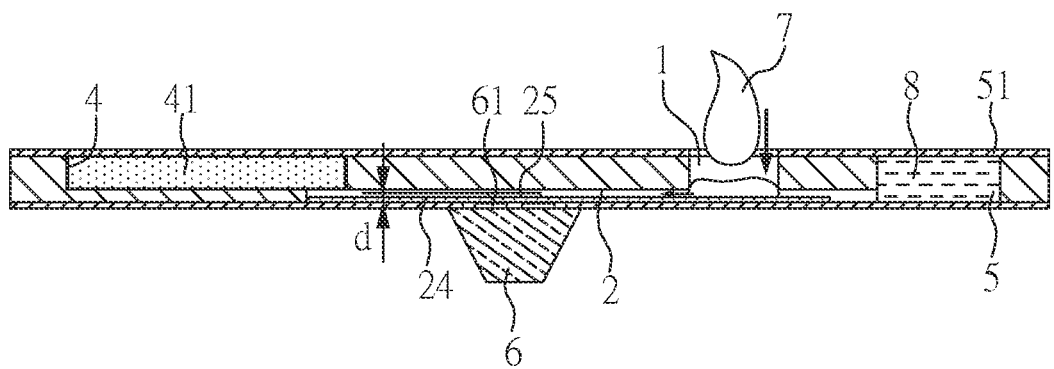
FIG. 3 shows a sectional view of the porous film microfluidic device according to Example 1 of the present invention.

Please refer to FIG. 1 in conjunction with FIG. 2 and FIG. 3. FIG. 1 shows an exploded view of the porous film microfluidic device according to Example 1 of the present invention. FIG. 2 shows a schematic view of the porous film microfluidic device according to Example 1 of the present invention. FIG. 3 shows a sectional view of the porous film microfluidic device according to Example 1 of the present invention. In this Example, the porous film microfluidic device comprised: a sample well 1; a porous film support structure 2, which comprised a first port 21 having a depth of 200-500 μm, a second port 22 and a third port 23 wherein the first port 21 is connected to the sample well 1, a porous film 24 was formed on the bottom of the porous film support structure 2, and a glass fiber film 25 was formed between the porous film support structure 2 and the porous film 24; a waste tank 4 connected to the second port 22 of the porous film support structure 2, wherein a water absorption element 41 was disposed in the waste tank 4, and a distance between the water absorption element 41 and the porous film 24 was 200-400 μm; a buffer solution tank 5 connected to the third port 23 of the porous film support structure 2 and sealed by a sealing film 51; and a COC (cycloolefin copolymer) plastic prism 6 disposed on the bottom of the porous film support structure 2, wherein the COC plastic prism 6 comprised a metal film 61 attached with a bio-molecule (not shown) and connected with the porous film 24, and a metal oxide layer 62 was formed on the COC plastic prism 6 and between the metal film 61 and COC plastic prism 6.

The porous film microfluidic device of this Example was made of polymethylmethacrylate (PMMA), but the microfluidic device is not limited thereto, and also may be transparent acrylate or the like. The sample well 1 in the microfluidic device, porous film support structure 2, the waste tank 4 and the buffer solution tank 5 were formed by conventional chemical etching, but they also can be formed by other methods. Furthermore, in this Example, the porous film was made of nitrocellulose (NC), the biomolecule was IFN-γ antibody, the metal film is made of gold (Au), and the water absorption element was made of non-woven fabric.

FIG. 3 shows a sectional view of the porous film microfluidic device of Example 1 taken along line A-A' of FIG. 2. The microfluidic device of this Example was used as follows: first, a sample 7 was injected into the sample well 1 of the microfluidic device, and then flowed into the porous film support structure 2 by the absorption of the porous film 3 and a hydraulic pressure difference between the sample well 1 and the waste tank 4, to reach the metal film 61, such that the target analyte in the sample 7 to be detected was combined with a biomolecule (not shown) of the metal film 61. Then, the sealing film 51 which sealed buffer solution tank 5 was punctured, such that the buffer solution 8 flowed into the porous film support structure 2 by the absorption of the porous film 3 and a hydraulic pressure difference between the buffer solution tank 5 and the waste tank 4, to wash the metal film 61, thereby washing out the excess sample which failed to combine with the biomolecule to prevent the detection from noise interference. Finally, the detection was achieved by placing the microfluidic device on a SPR detector to detect the change in the reflected signals of the metal film 61.

Example 2

Figure 4:
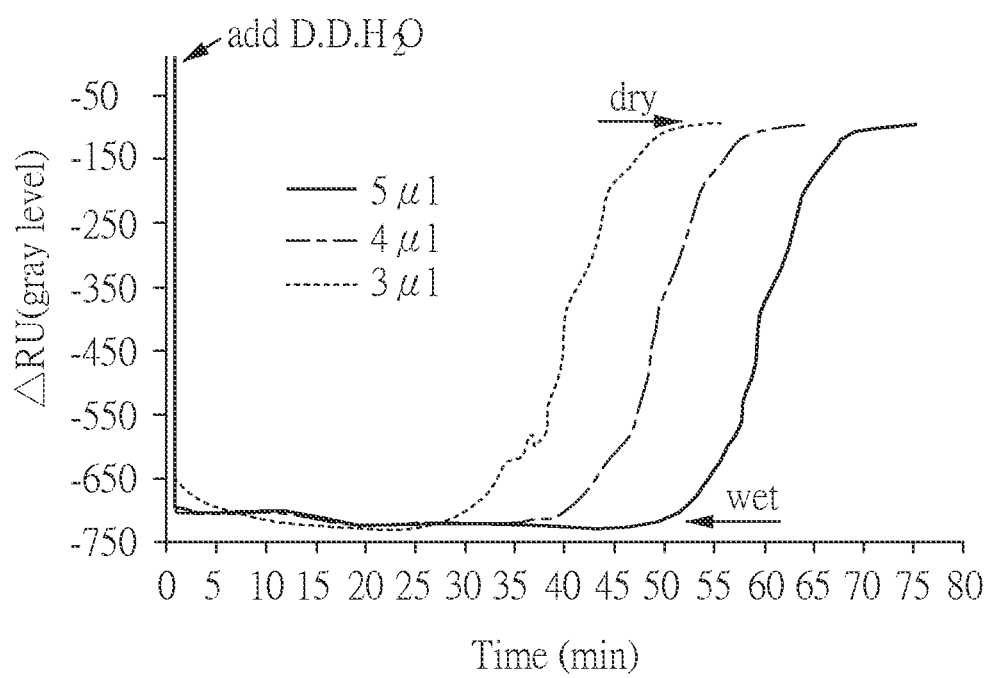
FIG. 4 shows a diagram of the detection result according to Example 2 of the present invention.

Stability Test with Control of Sample Evaporation Rate in Microfluidic Channel 5 μl, 4 μl, and 3 μl of D.D H2O were respectively prepared and dripped into the sample well of the microfluidic device of Example 1, followed by measuring the change in moisture content on the porous film by the SPR signals (ΔRU), and the result is shown in FIG. 4. The result in FIG. 4 indicates that the wetting time of the porous film for the 3 μl, 4 μl, and 5 μl sample reached up to approximately 30, 35, and 45 minutes, respectively. This Example conforms that the special design of the microfluidic device allows a 5 μl sample to maintain the wetting of the porous film support structure for up to nearly 45 minutes. In other words, the detection time for a 5 μl sample can be extended to 45 minutes.

Example 3

Detection of 3-IFN-γ Sample

First, the porous film of the microfluidic device in Example 1 was wetted by 5 μl of a TBE buffer solution, followed by dripping 20 μl of the IFN-γ liquid sample, a TBE buffer solution containing 0.1% triton, into the sample well, such that the sample flowed into the porous film support structure by the absorption of the porous film 3 and a hydraulic pressure difference between the sample well and the waste tank, and the excess sample was absorbed by the water absorption element of the waste tank. In this case, the porous film of this Example can merely absorb 5 μl of the sample. After that (about 3-10 seconds), the chemical agent (streptavidin in this Example) physically absorbed on the glass fiber sheet was dissolved and released by the liquid sample which resided in the porous material, for subjecting to a reaction together with the target analyte.

About 20 minutes later, the sealing film sealing the buffer solution tank was punctured, such that the TBE buffer solution flowed into the porous film support structure by the absorption of the porous film and a hydraulic pressure difference between the buffer solution tank and the waste tank, to wash out the excess sample. Then, the microfluidic device was subjected to the SPR detection, and the result indicated that the detection of IFN-r sample having a concentration of about 0.01 Nm can be completed within 25 minutes.

Example 4

Detection of Real Sample

A patient's plasma specimen can be detected in this Example. The experimental group was the blood plasma of the patient which has been confirmed to be infected by tuberculosis (TB), while the control group was the blood plasma of a healthy person.

P1 to P5 were five samples representing different patients respectively. Each sample included an experimental group (white, blood plasma of the TB patient) and a control group (black, blood plasma of the normal people). IFN-r interferon signal strength of each sample was detected by the porous film microfluidic device of Example 1.

Figure 5:
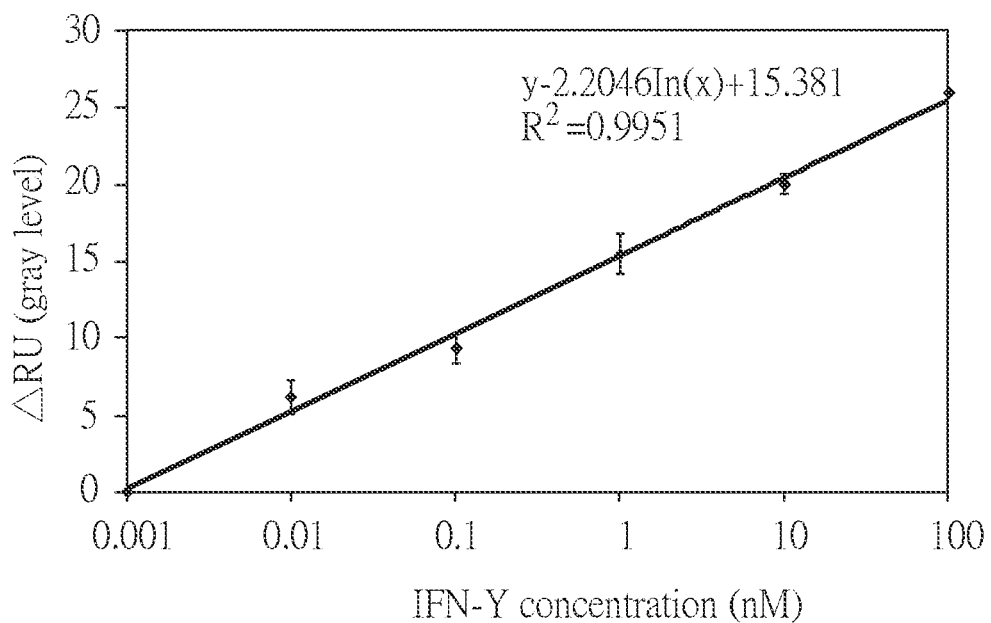
FIG. 5 is the standard curve according to Example 4 of the present invention.
Figure 6:
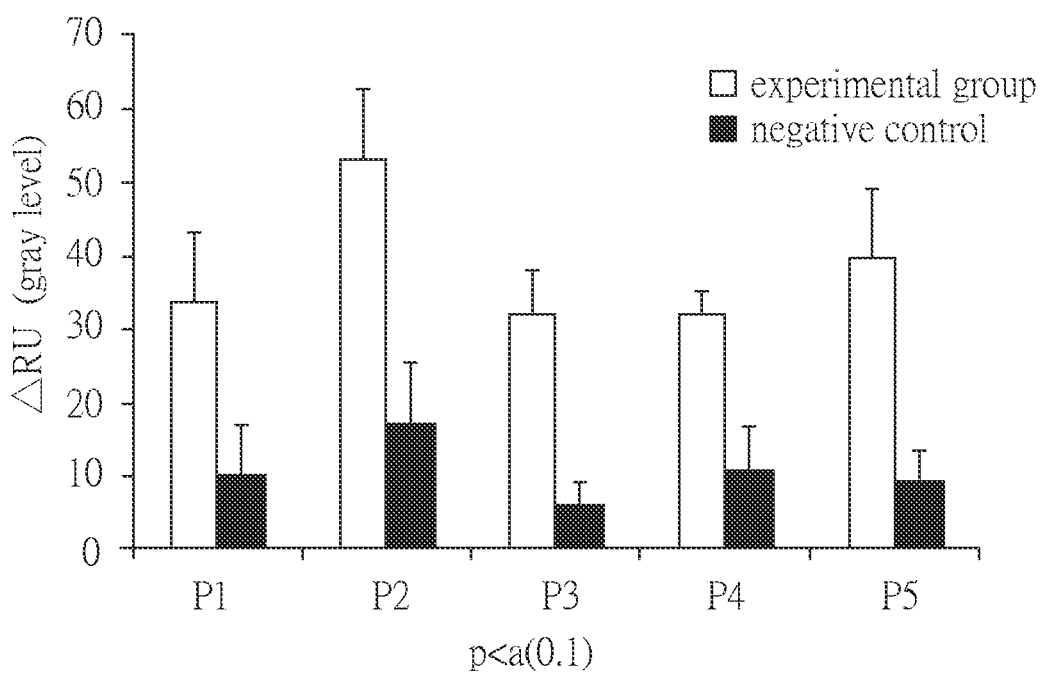
FIG. 6 shows a diagram of the detection result according to Example 4 of the present invention.

Please refer to FIG. 5 and FIG. 6. FIG. 5 is a standard curve according to this Example, which was obtained by dissolving the IFN-r interferon in PBS, wherein $R^2=0.9951$. FIG. 6 shows a schematic view of the detection result according to Example 4 of the present invention. From the results of the FIGs, it can be found that the IFN-r interferon signal strength of each of the P1 to P5 samples was 3-5 times stronger than that of the negative control group, indicating that the porous film microfluidic device of the present invention has a very high sensitivity, and can quickly detect the IFN-r interferon signals of target analyte in the samples.

From the results of the above Examples, it can be found that due to the special design of the porous film microfluidic device according to the present invention, not only the content of the specific component in trace amounts of sample can be detected by overcoming the evaporation problem of the trace amounts of sample, but also the detection sensitivity can be improved. Moreover, the content of the specific substance in the sample can be calculated based on the intensity changes of detected signal strength, thereby significantly improving the detection convenience.

Although the present invention has been explained in relation to its preferred embodiment, it is to be understood that many other possible modifications and variations can be made without departing from the spirit and scope of the invention as hereinafter claimed.

What is claimed is:

1. A porous film microfluidic device for surface plasmon resonance (SPR) quantitative analysis, comprising:
    a sample well;
    a porous film support structure, which comprises a first port having a width of 1-2 mm, a second port, and a third port, wherein the first port is connected to the sample well, a porous film is formed over the bottom of the porous film support structure, and a glass fiber film attached with a chemical agent is sandwiched between the porous film support structure and the porous film;
    a waste tank connected to the second port of the porous film support structure, wherein a water absorption element is disposed in the waste tank, and a vertical distance between a bottom surface of the water absorption element and a top surface of the porous film is 200-400 µm;
    a buffer solution tank connected to the third port of the porous film support structure and sealed by a sealing film; and
    a COC plastic prism disposed over the bottom of the porous film support structure, wherein the COC plastic prism comprises a metal film attached with a biomolecule and in contact with the porous film, and a metal oxide layer is formed over the COC plastic prism and between the metal film and COC plastic prism,
    wherein, a sample flows from the sample well into the porous film support structure to reach the metal film by a natural force, and a buffer solution flows from the buffer solution tank into the porous film support structure through the third port to reach the metal film by the natural force;
    wherein the water absorption element and the porous film are not in direct contact with each other and there is no intervening element disposed between the water absorption element and the porous film.

2. The porous film microfluidic device of claim 1, wherein the porous film has a volume of 5 µl to 10 µl.

3. The porous film microfluidic device of claim 1, wherein the porous film is made of nitrocellulose, hydrophilic wood pulp fiber, hydrophilic PVA fiber, a filament film or a non-woven fabric, and the porous film has a pore size of in the range of more than 10 to 500 µm.

4. The porous film microfluidic device of claim 1, wherein the biomolecule is DNA, RNA, a protein, an antibody, or combinations thereof.

5. The porous film microfluidic device of claim 1, wherein the metal film is made of Au or Ag.

6. The porous film microfluidic device of claim 1, wherein the metal film is a metal film array.

7. The porous film microfluidic device of claim 1, wherein the metal oxide layer is ZnO.

8. The porous film microfluidic device of claim 1, wherein the water absorption element is made of PVA foam.

9. The porous film microfluidic device of claim 1, wherein the natural force is a capillary force, a hydraulic pressure difference, a gravity force, an atmospheric pressure, or combinations thereof.

* * * * *